United States Patent
Okada et al.

(10) Patent No.: US 11,071,445 B2
(45) Date of Patent: Jul. 27, 2021

(54) MEDICAL LIGHT SOURCE DEVICE AND MEDICAL OBSERVATION SYSTEM

(71) Applicants: SONY OLYMPUS MEDICAL SOLUTIONS INC., Tokyo (JP); SONY CORPORATION, Tokyo (JP)

(72) Inventors: Naobumi Okada, Saitama (JP); Motoki Ozeki, Aichi (JP)

(73) Assignees: SONY OLYMPUS MEDICAL SOLUTIONS INC., Tokyo (JP); SONY CORPORATION, Tokyo (JP)

( * ) Notice: Subject to any disclaimer, the term of this patent is extended or adjusted under 35 U.S.C. 154(b) by 0 days.

(21) Appl. No.: 15/772,971

(22) PCT Filed: Jan. 11, 2017

(86) PCT No.: PCT/JP2017/000644
§ 371 (c)(1),
(2) Date: May 2, 2018

(87) PCT Pub. No.: WO2017/126388
PCT Pub. Date: Jul. 27, 2017

(65) Prior Publication Data
US 2018/0317758 A1    Nov. 8, 2018

(30) Foreign Application Priority Data

Jan. 19, 2016    (JP) .............................. JP2016-008082

(51) Int. Cl.
*A61B 1/06*    (2006.01)
*A61B 1/00*    (2006.01)
(Continued)

(52) U.S. Cl.
CPC ........ *A61B 1/0676* (2013.01); *A61B 1/00126* (2013.01); *A61B 1/04* (2013.01);
(Continued)

(58) Field of Classification Search
None
See application file for complete search history.

(56) References Cited

U.S. PATENT DOCUMENTS 6,413,207 B1 * 7/2002 Minami .................... A61B 1/04
348/221.1
6,635,011 B1 * 10/2003 Ozawa ............... A61B 1/00096
348/E5.029
(Continued)

FOREIGN PATENT DOCUMENTS

DE    3920494 A1    1/1991
EP    1413919 A1    4/2004
(Continued)

OTHER PUBLICATIONS

International Search Report dated Apr. 4, 2017 in PCT/JP2017/000644 filed Jan. 11, 2017.
(Continued)

*Primary Examiner* — Hung Q Dang
(74) *Attorney, Agent, or Firm* — Xsensus, LLP (57) ABSTRACT

[Object] To provide a medical light source device and a medical observation system capable of switching a light source while suppressing an increase in size and complication of a device.
[Solution] A medical light source device according to the present disclosure includes: a plurality of light sources; and a light source switching section that holds an end section of a light guide that transmits light, and is capable of disposing the end section on one of optical paths of light emitted by the plurality of light sources.

20 Claims, 7 Drawing Sheets

(51) Int. Cl.

| | | |
|---|---|---|
| *G02B 23/26* | (2006.01) | |
| *A61B 90/30* | (2016.01) | |
| *A61B 1/07* | (2006.01) | |
| *G02B 21/06* | (2006.01) | |
| *A61B 1/04* | (2006.01) | |
| *G02B 21/00* | (2006.01) | |
| *G02B 21/08* | (2006.01) | |
| *H04N 5/235* | (2006.01) | |
| *F21V 29/70* | (2015.01) | |
| *F21V 8/00* | (2006.01) | |
| *G02B 21/36* | (2006.01) | |
| *H04N 5/225* | (2006.01) | |

(52) U.S. Cl.
CPC .......... *A61B 1/0638* (2013.01); *A61B 1/0646* (2013.01); *A61B 1/0669* (2013.01); *A61B 1/0684* (2013.01); *A61B 1/07* (2013.01); *A61B 90/30* (2016.02); *G02B 21/0012* (2013.01); *G02B 21/06* (2013.01); *G02B 21/08* (2013.01); *G02B 23/26* (2013.01); *H04N 5/2354* (2013.01); *F21V 29/70* (2015.01); *G02B 6/0006* (2013.01); *G02B 21/36* (2013.01); *H04N 2005/2255* (2013.01)

(56) References Cited

U.S. PATENT DOCUMENTS

| | | | |
|---|---|---|---|
| 2003/0060682 A1* | 3/2003 | Handa | A61B 1/0669 600/178 |
| 2004/0090602 A1 | 5/2004 | Imade | |
| 2005/0284737 A1* | 12/2005 | Shitanaka | H01H 25/04 200/5 R |
| 2006/0152691 A1 | 7/2006 | Imade | |
| 2006/0244931 A1 | 11/2006 | Imade | |
| 2007/0038124 A1* | 2/2007 | Fulghum, Jr. | A61B 5/0071 600/476 |
| 2007/0109501 A1 | 5/2007 | Imade | |
| 2007/0121086 A1 | 5/2007 | Imade | |
| 2009/0312607 A1* | 12/2009 | Sunagawa | A61B 1/0638 600/160 |
| 2010/0039507 A1* | 2/2010 | Imade | A61B 1/00165 348/68 |
| 2010/0271697 A1* | 10/2010 | Nakamura | G02B 5/208 359/390 |
| 2011/0032383 A1 | 2/2011 | Imade | |
| 2011/0063427 A1* | 3/2011 | Fengler | A61B 1/00186 348/65 |
| 2011/0286212 A1 | 11/2011 | Furuta | |
| 2014/0010424 A1* | 1/2014 | Chiba | A61B 1/00009 382/128 |
| 2015/0109777 A1* | 4/2015 | Feng | F21V 29/508 362/235 |
| 2016/0344162 A1* | 11/2016 | Konno | C03B 23/20 |

FOREIGN PATENT DOCUMENTS

| | | |
|---|---|---|
| JP | 54-145989 U | 10/1979 |
| JP | 1-284822 A | 11/1989 |
| JP | 4-117611 U | 10/1992 |
| JP | 6-243707 A | 9/1994 |
| JP | H09-015514 A | 1/1997 |
| JP | 10-165367 A | 6/1998 |
| JP | 2000-276925 A | 10/2000 |
| JP | 2004-187986 A | 7/2004 |
| JP | 2006-34560 A | 2/2006 |
| JP | 2009136581 A | 6/2009 |

OTHER PUBLICATIONS

Extended European Search Report dated Aug. 28, 2019, issued in corresponding European Application No. 17741268.1, 7 pages.

* cited by examiner

MEDICAL LIGHT SOURCE DEVICE AND MEDICAL OBSERVATION SYSTEM

TECHNICAL FIELD

The present disclosure relates to a medical light source device and a medical observation system.

BACKGROUND ART

Conventionally, in a medical observation system that images an object using an image sensor and observes the object, a light source device that emits illumination light for illuminating an object has been used (for example, see Patent Literature 1). The light source device disclosed by Patent Literature 1 includes a main light source, an auxiliary light source, and a light guide, and when the main light source deteriorates and the amount of light becomes small, it can be switched to the auxiliary light source. In the light source device disclosed by Patent Literature 1, an incident end of the light guide and the main light source are fixed, and illumination light is switched to the auxiliary light source by moving the auxiliary light source to between the incident end of the light guide and the main light source.

CITATION LIST

Patent Literature

Patent Literature 1: JP 2004-187986A

DISCLOSURE OF INVENTION

Technical Problem

However, in the light source device disclosed by Patent Literature 1, the light source is switched by moving the auxiliary light source to between the incident end of the light guide and the main light source, which requires an actuator or the like for moving the auxiliary light source. This brings about a problem of an increase in size and complication of the light source device.

In view of the above, an object of the present disclosure is to provide a medical light source device and a medical observation system capable of switching a light source while suppressing an increase in size and complication of a device.

Solution to Problem

In order to solve the above-mentioned problem and achieve the object, a medical light source device according to the present disclosure includes: a plurality of light sources; and a light source switching section that holds an end section of a light guide that transmits light, and is capable of disposing the end section on one of optical paths of light emitted by the plurality of light sources.

In addition, in the medical light source device according to the present disclosure, the plurality of light sources may include a main light source and an auxiliary light source.

In addition, in the medical light source device according to the present disclosure, the main light source and the auxiliary light source may have substantially a same maximum luminance.

In addition, in the medical light source device according to the present disclosure, the main light source and the auxiliary light source may each emit white light.

In addition, the medical light source device according to the present disclosure may further include a collimator lens that makes light emitted by the light source into substantially parallel light. The light source switching section may include a condenser lens that condenses the parallel light on the end section of the light guide.

In addition, the medical light source device according to the present disclosure may further include a power supply section that supplies electric power to the plurality of light sources. The main light source and the auxiliary light source may have different power supply systems.

In addition, the medical light source device according to the present disclosure may further include a heat sink that absorbs heat of the plurality of light sources.

In addition, a medical observation system according to the present disclosure includes: an imaging device that captures an enlarged image of a minute area of an object and generates an imaging signal; a light guide that transmits illumination light to the imaging device; and a medical light source device including a plurality of light sources that emit the illumination light, and a light source switching section that holds an incident end of the light guide, and disposes the incident end on one of optical paths of the illumination light emitted by the plurality of light sources, thereby switching the light source of illumination light that enters the light guide.

Advantageous Effects of Invention

According to the present disclosure, an effect of being able to switch a light source while suppressing an increase in size and complication of a device is obtained.

MODE(S) FOR CARRYING OUT THE INVENTION

Modes for carrying out the present disclosure (hereinafter referred to as "embodiments") are described below. The embodiments describe, as examples of a medical observation system including a medical light source device according to the present disclosure, a surgical microscope system and an endoscope device that capture and display an image of the interior of a subject such as a patient. In addition, these embodiments do not limit the present disclosure. Further-more, in description of the drawings, the same portions are denoted by the same reference numeral.

Embodiment 1

Figure 1:
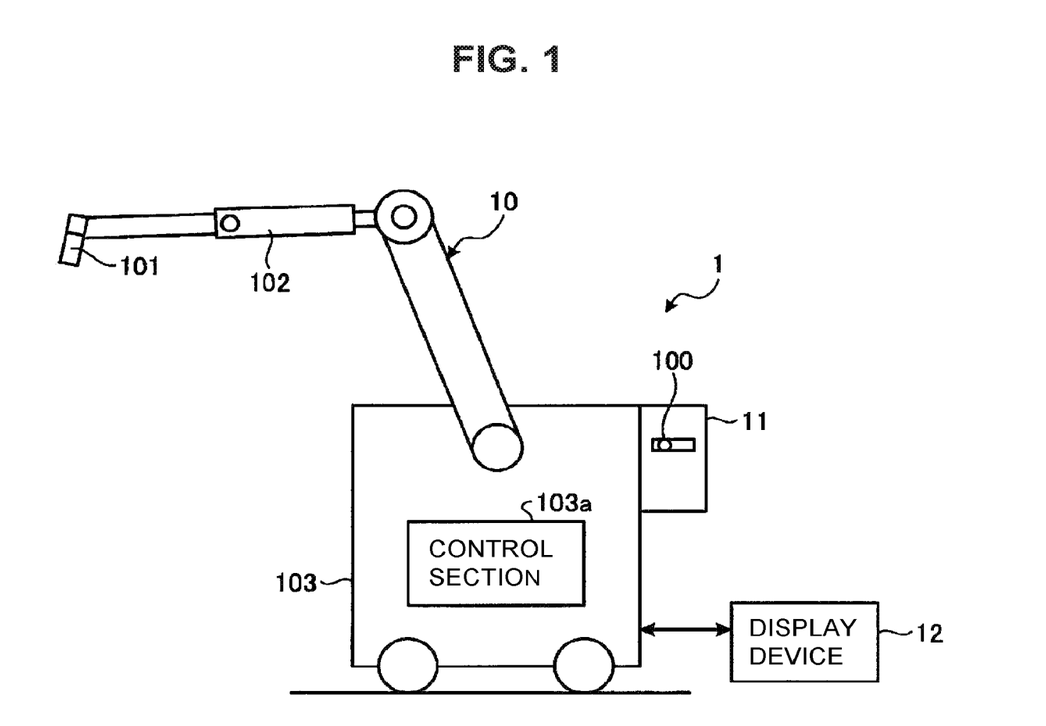
FIG. 1 schematically illustrates an overall configuration of a surgical microscope system, which is a medical observation system including a medical light source device, according to Embodiment 1 of the present disclosure.

FIG. 1 schematically illustrates an overall configuration of a surgical microscope system, which is a medical observation system including a medical light source device, according to Embodiment 1 of the present disclosure. The surgical microscope system according to the Embodiment 1 captures an enlarged image of a predetermined field-of-view region illuminated by illumination light, and displays the captured image.

A surgical microscope system 1 includes a microscope device 10, which is a medical imaging device that acquires an image for observing an object by imaging, a light source device 11 (medical light source device) that is installed on the microscope device 10 and emits illumination light for illuminating an object, and a display device 12 that displays an image captured by the microscope device 10. Note that the display device 12 can be integrated with the microscope device 10. The display device 12 displays an image acquired by the microscope device 10. The display device 12 is preferably, but not limited to, one with a display section of 55 inches or more so that a sense of immersion is easily obtained in observation.

The microscope device 10 includes a microscope section 101 that captures an enlarged image of a minute area of an object, a support section 102 including an arm that is connected to a base end section of the microscope section 101 and supports the microscope section 101 so as to allow revolution, and a base section 103 that holds a base end section of the support section 102 so as to allow revolution and is movable on the floor. The base section 103 includes a control section 103a that controls operation of the surgical microscope system 1. Note that the base section 103 may be, instead of being provided on the floor to be movable, configured to be fixed on the ceiling, a wall surface, or the like to support the support section 102. In addition, the microscope device 10 applies illumination light emitted by the light source device 11 to an object via a light guide (not illustrated). The microscope device 10 supplies externally supplied electric power to each section and the light source device 11.

The microscope section 101 is cylindrical, for example, and includes an imaging section in its interior. A side surface of the microscope section 101 is provided with a switch that accepts input of an operation instruction for the microscope device 10. An aperture at a lower end section of the microscope section 101 is provided with a cover glass to protect in the interior (not illustrated).

Under the control of the control section 103a, the imaging section images an object. This imaging section includes an image sensor, such as a charge coupled device (CCD) or a complementary metal oxide semiconductor (CMOS), that receives an object image formed by an optical system (not illustrated) and converts it into an electrical signal. In the case of the CCD, for example, a signal processing section (not illustrated) that performs signal processing (e.g. A/D conversion) on an electrical signal (analog signal) from the image sensor and outputs an imaging signal is mounted on a sensor chip or the like. In the case of the CMOS, for example, a signal processing section that performs signal processing (e.g. A/D conversion) on an electrical signal (analog) obtained by converting light and outputs an imaging signal is included in the image sensor.

The microscope device 10 performs noise reduction, and signal processing such as A/D conversion as necessary, on an imaging signal output by the microscope section 101 to generate a digitalized imaging signal (pulse signal), and generates an image signal for display to be displayed by the display device 12. The microscope device 10 performs predetermined signal processing on the imaging signal to generate an image signal for display that includes an object image. Here, examples of image processing include various types of image processing such as interpolation processing, color correction processing, color enhancement processing, and edge enhancement processing.

In addition, the microscope device 10 generates a synchronization signal for the microscope device 10, the light source device 11, and the display device 12, and a clock. The synchronization signal (e.g., a synchronization signal indicating imaging timing by the microscope section 101, or the like) and the clock (e.g., a clock for serial communication) are transmitted via lines (not illustrated), and the microscope section 101 and the like are driven on the basis of the synchronization signal and clock.

A user, such as a surgeon, moves the microscope section 101 and performs zoom operation while operating various switches in a state of gripping the microscope section 101. Note that the shape of the microscope section 101 is preferably a slender shape extending in an observation direction so that the user can easily grip the microscope section 101 and change a field-of-view direction. Therefore, the shape of the microscope section 101 may be a shape other than a cylinder, and may be, for example, a polygonal column.

The control section 103a performs drive control over each constituent section of the surgical microscope system 1, information input/output control over each constituent section, and the like. The control section 103a generates a control signal with reference to communication information data (e.g., communication format information or the like) recorded in a memory, and sends the generated control signal to each section.

In addition, the control section 103a outputs a control signal, such as an instruction to switch a light source or an instruction related to an amount of light, to the light source device 11.

Note that the control section 103a is implemented by using a general-purpose processor such as a central processing unit (CPU) including an internal memory (not illustrated) on which a program is recorded, or a dedicated processor such as various arithmetic circuits that execute a specific function such as an application specific integrated circuit (ASIC). In addition, the control section 103a may include a field programmable gate array (FPGA; not illustrated), which is a type of programmable integrated circuit. Note that in the case where the control section 103a includes a FPGA, a memory that stores configuration data may be provided, and the FPGA, which is a programmable integrated circuit, may be configured by using configuration data read from the memory.

Figure 2:
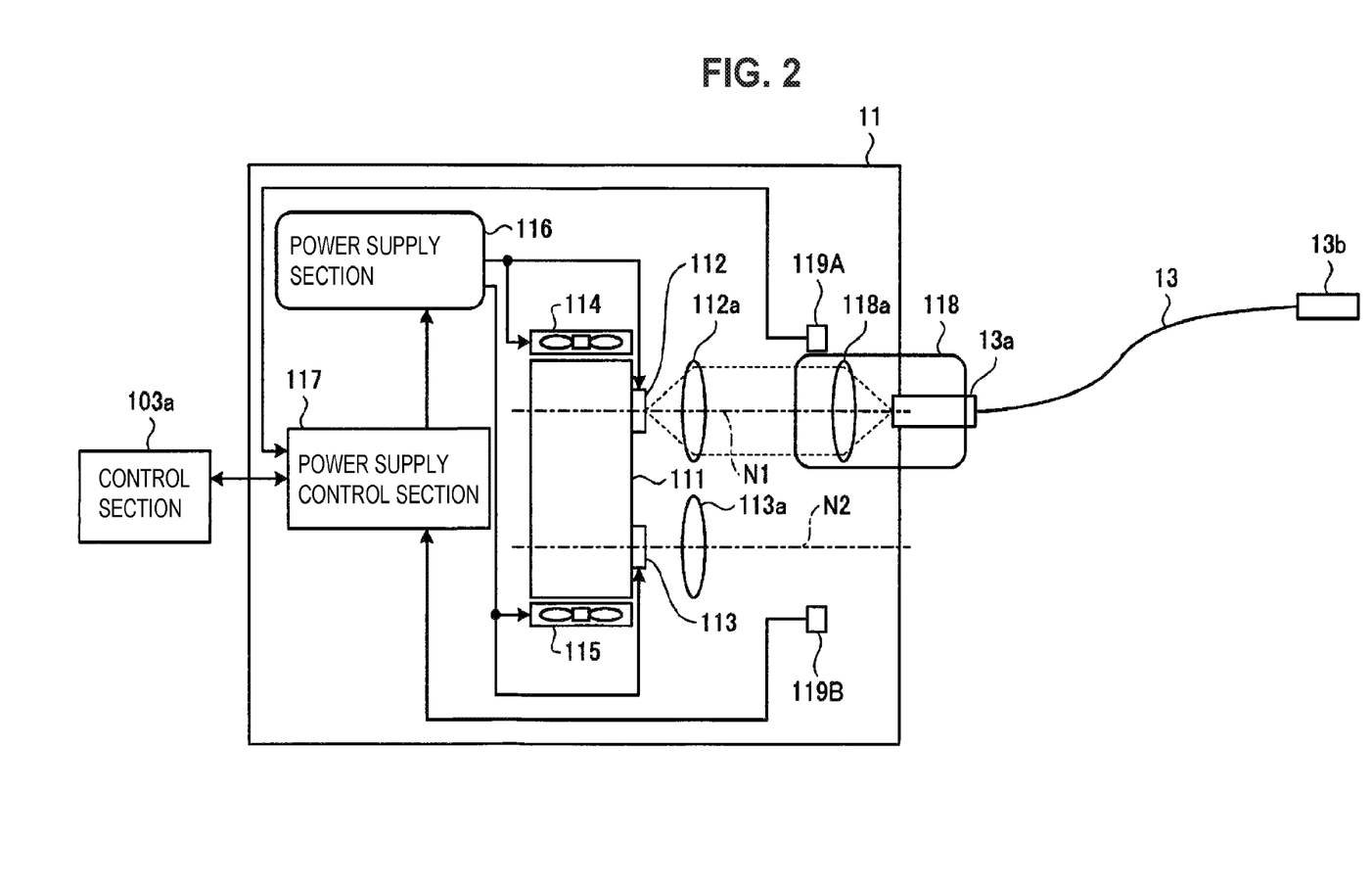
FIG. 2 is a schematic diagram illustrating a configuration of the light source device illustrated in FIG. 1.

FIG. 2 is a schematic diagram illustrating a configuration of the light source device illustrated in FIG. 1, and illustrates a case where light emitted by a first light source 112 serving as a main light source is emitted as illumination light. The light source device 11 detachably holds one end of a light guide 13, and supplies white illumination light for illuminating the interior of a living body to the one end of the light guide 13. An incident end 13a of the light guide 13, which is the one end where illumination light enters, is detachably connected to the light source device 11, and an emission end 13b, which is the other end that emits illumination light, is detachably connected to the microscope device 10. Thus, the light guide 13 transfers light supplied from the light source device 11 from the one end to the other end, and supplies illumination light to the microscope device 10 via the emission end 13*b*. The microscope device 10 emits illumination light supplied via the light guide 13 from the microscope section 101 to illuminate a subject.

The light source device 11 includes a heat sink 111, the first light source 112, a second light source 113, a first fan 114, a second fan 115, a power supply section 116, a power supply control section 117, and a light source switching section 118. In the Embodiment 1, the power supply section 116, the power supply control section 117, and the light source switching section 118 constitute a light source switching means.

The heat sink 111 includes, for example, plate-like members formed using a material with high heat transfer characteristics stacked at predetermined intervals. The heat sink 111 is not limited to this configuration, as long as it has a large surface area and high heat dissipation characteristics. For example, the heat sink 111 may be a plurality of rod-like members provided to stand, or may have a bellows shape.

The first light source 112 is a main light source that is mainly used, and is implemented by using a high-luminance light emitting diode (LED) package that emits white light. The first light source 112 is caused to emit illumination light by electric power supplied from the power supply section 116.

The first light source 112 is provided with a first collimator lens 112*a* on an optical path N1 of illumination light emitted by the first light source 112. The first collimator lens 112*a* is disposed in a manner that its own focus position is located on a light-emitting surface of the first light source 112, and converts illumination light emitted by the first light source 112 into parallel light.

The second light source 113 is an auxiliary light source that is used in the case where the main light source is unavailable, and is implemented by using a high-luminance LED package that emits white light. The second light source 113 is caused to emit illumination light by electric power supplied from the power supply section 116. In the Embodiment 1, description is given assuming that the first light source 112 and the second light source 113 are high-luminance LED packages of the same type, for example, having the same maximum luminance. Note that a halogen lamp or a xenon lamp may be used as the light source, and the first light source 112 and the second light source 113 may be different types of light sources. In addition, in the Embodiment 1, the first light source 112 and the second light source 113 may have substantially the same maximum luminance, for example, when one has a luminance of 1, the other may have a luminance of approximately 0.9 to 1.1.

The second light source 113 is provided with a second collimator lens 113*a* on an optical path N2 of illumination light emitted by the second light source 113. The second collimator lens 113*a* is disposed in a manner that its own focus position is located on a light-emitting surface of the second light source 113, and converts illumination light emitted by the second light source 113 into parallel light.

The first light source 112 and the second light source 113 are arranged side by side with respect to the heat sink 111. In addition, the first light source 112 and the second light source 113 are fixed to be thermally connected to a surface of the heat sink 111. Specifically, the first light source 112 and the second light source 113 may be fixed to the heat sink 111 via a sheet-like member with high thermal conductivity, such as graphite, or thermal conduction grease, or may be directly fixed to the surface of the heat sink 111.

The first fan 114 is provided on the first light source 112 side of the heat sink 111. The first fan 114 is rotated by electric power supplied from the power supply section 116, thereby playing an auxiliary role of releasing heat of the heat sink 111 to the exterior.

The second fan 115 is provided on the second light source 113 side of the heat sink 111. The second fan 115 is rotated by electric power supplied from the power supply section 116, thereby playing an auxiliary role of releasing heat of the heat sink 111 to the exterior.

The power supply section 116 supplies electric power supplied from the microscope device 10 to the first light source 112 and the first fan 114, or the second light source 113 and the second fan 115. Under the control of the power supply control section 117, the power supply section 116 selects a member to which electric power is to be supplied, and also supplies electric power corresponding to a control signal, thereby adjusting the amount of light of the light source.

The power supply control section 117 selects a member (the first light source 112 and the first fan 114, or the second light source 113 and the second fan 115) to which electric power is to be supplied by the power supply section 116 according to detection results of a first detection sensor 119A and a second detection sensor 119B described later, and also inputs a control signal for adjusting electric power to be supplied to the light source to the power supply section 116, in accordance with a control signal input from the microscope device 10 (the control section 103*a*).

The light source switching section 118 detachably holds the incident end 13*a* of the light guide 13, and is provided to be movable to one of a position (e.g., a first position) of illumination light emitted by the first light source 112 on the optical path N1 and a position (e.g., a second position) of illumination light emitted by the second light source 113 on the optical path N2. A movement mechanism that moves the light source switching section 118 is implemented by using a mechanism that causes sliding using a linear guide or a mechanism that causes movement of a position by rotation. In addition, the light source switching section 118 is configured to be positionable and movable by a click mechanism, urging force of a spring, or the like, and is disposed at one of on the optical path N1 of illumination light emitted by the first light source 112 and on the optical path N2 of illumination light emitted by the second light source 113. Movement of the light source switching section 118 switches illumination light to enter the light guide 13.

The light source switching section 118 is provided with a condenser lens 118*a* that condenses parallel light generated by the first collimator lens 112*a* or the second collimator lens 113*a* on the incident end 13*a* of the light guide 13. That is, the light source switching section 118 moves the condenser lens 118*a* and the incident end 13*a* by its own movement to switch parallel light (illumination light) to be condensed by the condenser lens 118*a*.

The first detection sensor 119A and the second detection sensor 119B are implemented by using, for example, a photo-interrupter or a proximity sensor, and input a detection signal to the power supply control section 117 in the case where the light source switching section 118 comes close. The first detection sensor 119A is disposed at a position such that the first detection sensor 119A is close to the light source switching section 118 and generates a detection signal in the case where the light source switching section 118 is located at the first position. In addition, the second detection sensor 119B is disposed at a position such that the second detection sensor 119B is close to the light source switching section 118 and generates a detection signal in the case where the light source switching section 118 is located at the second position.

The power supply control section 117 determines a position of the light source switching section 118 on the basis of a detection signal that is input, and selects light sources to be turned on and turned off and fans to be driven and stopped by supply from the power supply section 116. Note that the power supply control section 117 may control on and off of the light source as an analog circuit.

Figure 3:
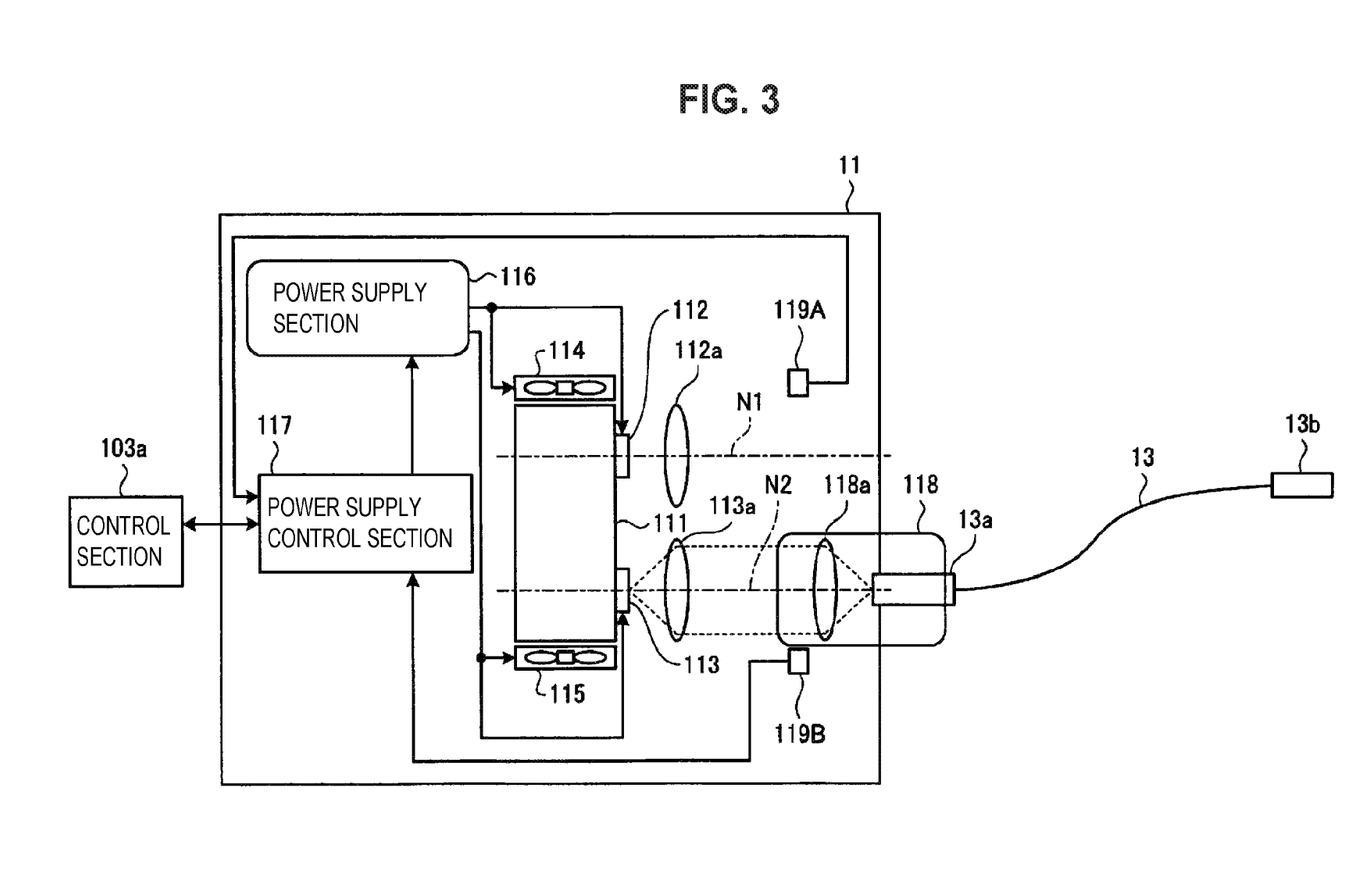
FIG. 3 is a schematic diagram illustrating a configuration of the light source device illustrated in FIG. 1.

FIG. 3 is a schematic diagram illustrating a configuration of the light source device illustrated in FIG. 1, and illustrates a case where light emitted by the second light source 113 serving as an auxiliary light source is emitted as illumination light. When the light source switching section 118 is moved from the state where illumination light emitted by the first light source 112 enters as illustrated in FIG. 2, the state is switched to a state where illumination light emitted by the second light source 113 enters as illustrated in FIG. 3. This movement operation of the light source switching section 118 can be implemented by moving a lever 100 (see FIG. 1), for example. Note that movement of the light source switching section 118 may be controlled by the control section 103a or the power supply control section 117.

When the light source switching section 118 moves, a detection signal is input to the power supply control section 117 by a detection sensor, and under the control of the power supply control section 117, electric power to be supplied from the power supply section 116 is changed, and a light source to emit illumination light and a fan to be driven are switched. Specifically, in the case of transition to the state of FIG. 3, the state of FIG. 2 in which illumination light is emitted from the first light source 112 and the first fan 114 is driven is switched to the state of FIG. 3 in which illumination light is emitted from the second light source 113 and the second fan 115 is driven. Note that in the case where one light source is emitting light, the other light source is off.

According to the above-described Embodiment 1, in a configuration in which a light source of illumination light is switched by causing illumination light emitted by one light source, of illumination light emitted from two light sources, to enter the incident end 13a of the light guide 13, the light source switching section 118 that holds the incident end 13a of the light guide 13 and includes the condenser lens 118a is moved to switch illumination light to be caused to enter the incident end 13a; thus, it is possible to switch a light source while suppressing an increase in size and complication of a device, as compared with a configuration in which a light source is moved by an actuator or the like as in a conventional configuration.

In addition, according to the above-described Embodiment 1, the light source switching section 118 is moved with the lever 100 or the like to switch illumination light; thus, illumination light can be switched further easily.

In the surgical microscope system 1 according to the Embodiment 1, in the case where illumination light provided by the first light source 112 becomes unavailable during surgery, for example, a surgeon, such as a doctor or a nurse, switches the light source switching section 118 from the first position to the second position. Possible reasons for illumination light provided by the first light source 112 becoming unavailable are deterioration, failure, and the like of the light source. When the light source switching section 118 is moved from the first position to the second position, electric power supply to the first light source 112 by the power supply section 116 is shut off. Instead, the second fan 115 rotates and the second light source 113 is turned on. Illumination light from the second light source 113 is caused to enter the incident end 13a of the light guide 13 by the second collimator lens 113a and the condenser lens 118a. In this manner, a light source of the same type as the first light source 112 that is normally used is installed as the second light source 113 for backup; thus, the same amount of light as that of the main light source can be output when the light source is switched to the backup light source. Consequently, even if the light source is switched to the backup light source during surgery, surgery can be continued under the same brightness and/or color as that of the main light source.

In addition, according to the above-described Embodiment 1, using the same high-luminance LED package for the first light source 112 and the second light source 113 makes conditions of light-emitting surfaces the same, so that commonality of specifications of the first collimator lens 112a and the second collimator lens 113a can be provided, which can simplify design and procurement.

In addition, according to the above-described Embodiment 1, fixing the first light source 112 and the second light source 113 to the common heat sink 111 can reduce the size of the light source device 11. Assuming that the first light source 112 and the second light source 113 are not on simultaneously, a volume of the heat sink 111 needed for cooling may be any size that is sufficient for cooling heat of the light source when the first light source 112 or the second light source 113 alone is on. In contrast, in the case where the first light source 112 and the second light source 113 are fixed to separate heat sinks, each of them requires a size for cooling heat, which makes the light source device itself large.

In addition, according to the above-described Embodiment 1, if a light-emitting surface size of the high-luminance LED package used for the first light source 112 and the second light source 113 is substantially the same as an effective diameter size of the incident end 13a of the light guide 13, commonality of specifications of the first collimator lens 112a, the second collimator lens 113a, and the condenser lens 118a can be provided. By thus providing commonality of parts, labor saving in design and a reduction in cost of parts can be achieved.

Note that although the above-described Embodiment 1 gives description assuming that light control is performed by a control signal from the control section 103a, the light source device 11 may be provided with an adjustment knob, and light control of the light source may be performed by operating the adjustment knob.

In addition, although the above-described Embodiment 1 gives description assuming that one power supply section 116 supplies electric power to the first light source 112, the second light source 113, the first fan 114, and the second fan 115, there may be provided a power supply section that supplies electric power to the first light source 112 and the first fan 114, and a power supply section that supplies electric power to the second light source 113 and the second fan 115, for example.

In addition, although the above-described Embodiment 1 gives description assuming that the light source switching section 118 includes the condenser lens 118a and holds the incident end 13a, the condenser lens 118a may be provided outside the light source switching section 118, and the light source switching section 118 may hold only the incident end 13a and move only the incident end 13a. In this case, a condenser lens is provided for each of the first collimator lens 112a and the second collimator lens 113a.

In addition, although the above-described Embodiment 1 gives description assuming that the light source switching section 118 is moved with the lever 100 or the like to switch the light source, an amount of illumination light that enters the light guide 13 may be detected, and the light source switching section 118 may be moved to switch the light source in the case where the amount of light is smaller than a predetermined amount of light. In addition, a notification may be issued by sound, light, an image, or the like when the light source is switched.

(Modification 1 of Embodiment 1)

Figure 4:
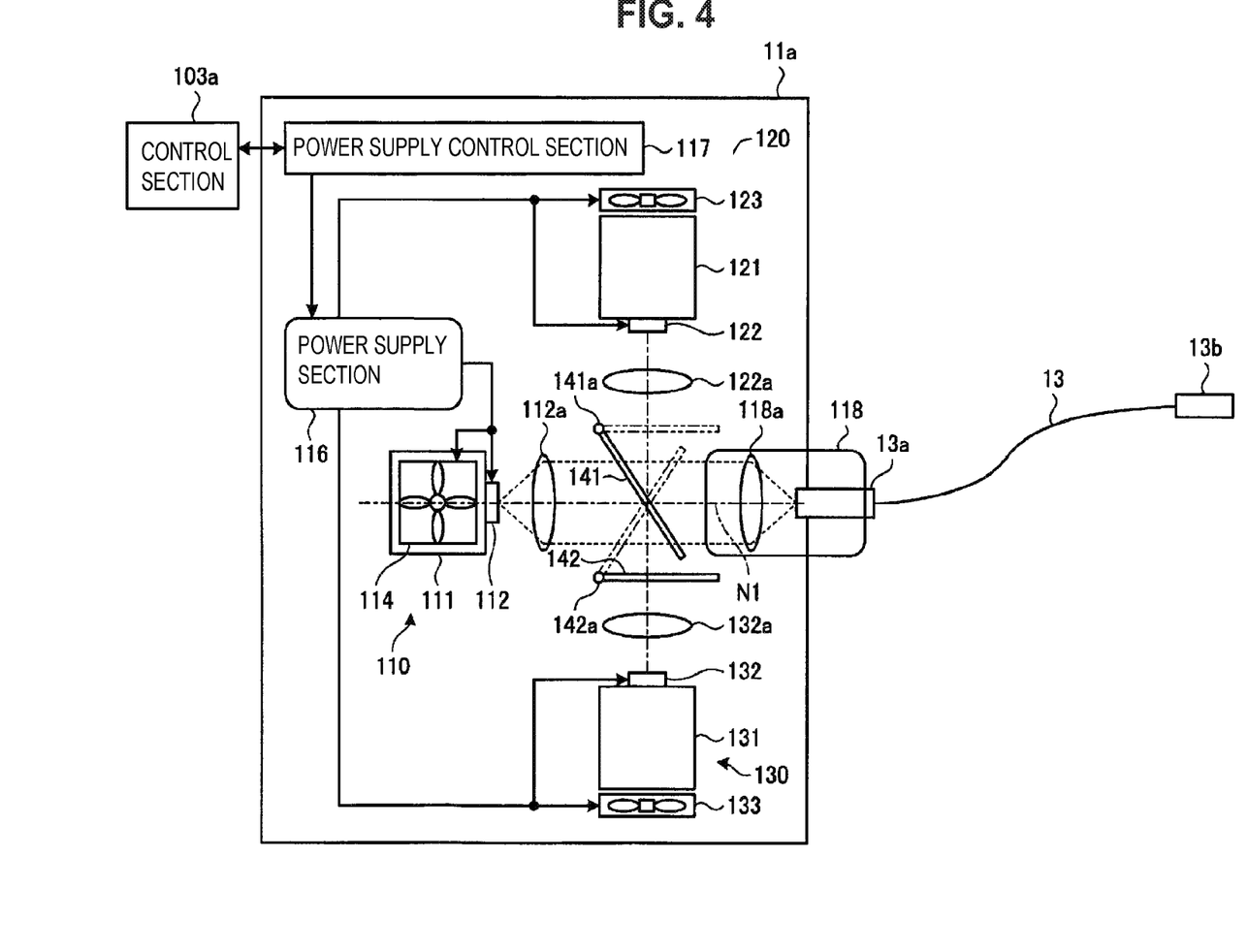
FIG. 4 is a schematic diagram illustrating a configuration of a light source device according to Modification 1 of Embodiment 1 of the present disclosure.

Now, Modification 1 of Embodiment 1 of the present disclosure will be described. Although the above-described Embodiment 1 gives description assuming that the main light source is one light source, i.e., the first light source 112, a plurality of light sources are provided as the main light sources in the Modification 1. FIG. 4 is a schematic diagram illustrating a configuration of a light source device according to Modification 1 of Embodiment 1 of the present disclosure, as seen from the first fan 114 side in a movement direction of the light source switching section 118. That is, the second light source 113 and the like are present in a depth direction orthogonal to the page of FIG. 4. Note that the same configuration as that described above is denoted by the same reference numeral for description.

As illustrated in FIG. 4, a light source device 11a according to the Modification 1 includes, as main light sources, a first main light source section 110 including the heat sink 111, the first light source 112 (referred to as the first main light source 112 in the Modification 1), and the first fan 114 described above, a second main light source section 120 including a second heat sink 121, a second main light source 122, and a third fan 123, and a third main light source section 130 including a third heat sink 131, a third main light source 132, and a fourth fan 133. In the Modification 1, the light source device 11a additionally includes the configuration according to the above-described Embodiment 1, for example, the second light source 113, the power supply section 116, the power supply control section 117, and the light source switching section 118.

The second main light source 122 is implemented by using a high-luminance LED package that emits light of a near infrared wavelength band (e.g., 700 nm to 800 nm). The second main light source 122 is caused to emit illumination light by electric power supplied from the power supply section 116. The second main light source 122 is provided with a third collimator lens 122a on an optical path of illumination light emitted by the second main light source 122.

The third main light source 132 is implemented by using a high-luminance LED package that emits light of a wavelength band including ultraviolet and part of purple (e.g., 390 nm to 470 nm). The third main light source 132 is caused to emit illumination light by electric power supplied from the power supply section 116. The third main light source 132 is provided with a fourth collimator lens 132a on an optical path of illumination light emitted by the third main light source 132.

In addition, the light source device 11a includes a mirror 141 and a dichroic mirror 142. The mirror 141 is rotatable about a rotation shaft 141a, and is provided to be able to be inserted and removed into/from an optical path of illumination light of the first main light source 112. The dichroic mirror 142 is rotatable about a rotation shaft 142a, and is provided to be able to be inserted and removed into/from the optical path of illumination light of the first main light source 112. The dichroic mirror 142 transmits light of a partial wavelength band (narrow band: 530 nm to 550 nm) of a green wavelength band, and reflects light of a wavelength band other than this.

In accordance with a control signal from the control section 103a, the power supply control section 117 selects the main light source section to be driven and causes the power supply section 116 to supply electric power, and also controls driving of the mirror 141 or the dichroic mirror 142. An example of input timing of the control signal is a timing at which an observation mode is changed by switching of a filter in the microscope section 101, or the like.

For example, in the case where the power supply section 116 drives the second main light source section 120, near infrared light is emitted from the second main light source 122 and the third fan 123 is driven, and also, the power supply control section 117 performs control to insert the mirror 141 into the optical path of illumination light of the first main light source 112. Thus, the mirror 141 can cause infrared light to travel along the optical path N1 and reflect it toward the light source switching section 118 to cause the near infrared light to enter the incident end 13a.

In addition, in the case of causing the light source device 11a to emit narrow-band light to perform narrow-band light observation using the microscope device 10, the power supply section 116 drives the first main light source section 110 and the third main light source section 130, so that light is emitted from the first main light source 112 and the third main light source 132, and the first fan 114 and the third fan 123 are driven, and also, the power supply control section 117 performs control to insert the dichroic mirror 142 into the optical path of illumination light of the first main light source 112. Thus, the dichroic mirror 142 can transmit narrow-band light of 530 nm to 550 nm and reflect light of a wavelength band of 390 nm to 470 nm, to cause light (narrow-band light) of wavelength bands of 390 nm to 470 nm and 530 nm to 550 nm to travel along the optical path N1 to enter the light source switching section 118 (the incident end 13a).

In addition, in the case of causing white light provided by the first main light source 112 to enter the light source switching section 118, the mirror 141 and the dichroic mirror 142 may be caused to retreat from the optical path of illumination light of the first main light source 112, and the first main light source 112 may be caused to emit white light.

According to the Modification 1, an effect similar to that of the above-described Embodiment 1 can be obtained, and also, a wavelength band of illumination light to be emitted can be switched selectively in the main light source.

(Modification 2 of Embodiment 1)

Figure 5:
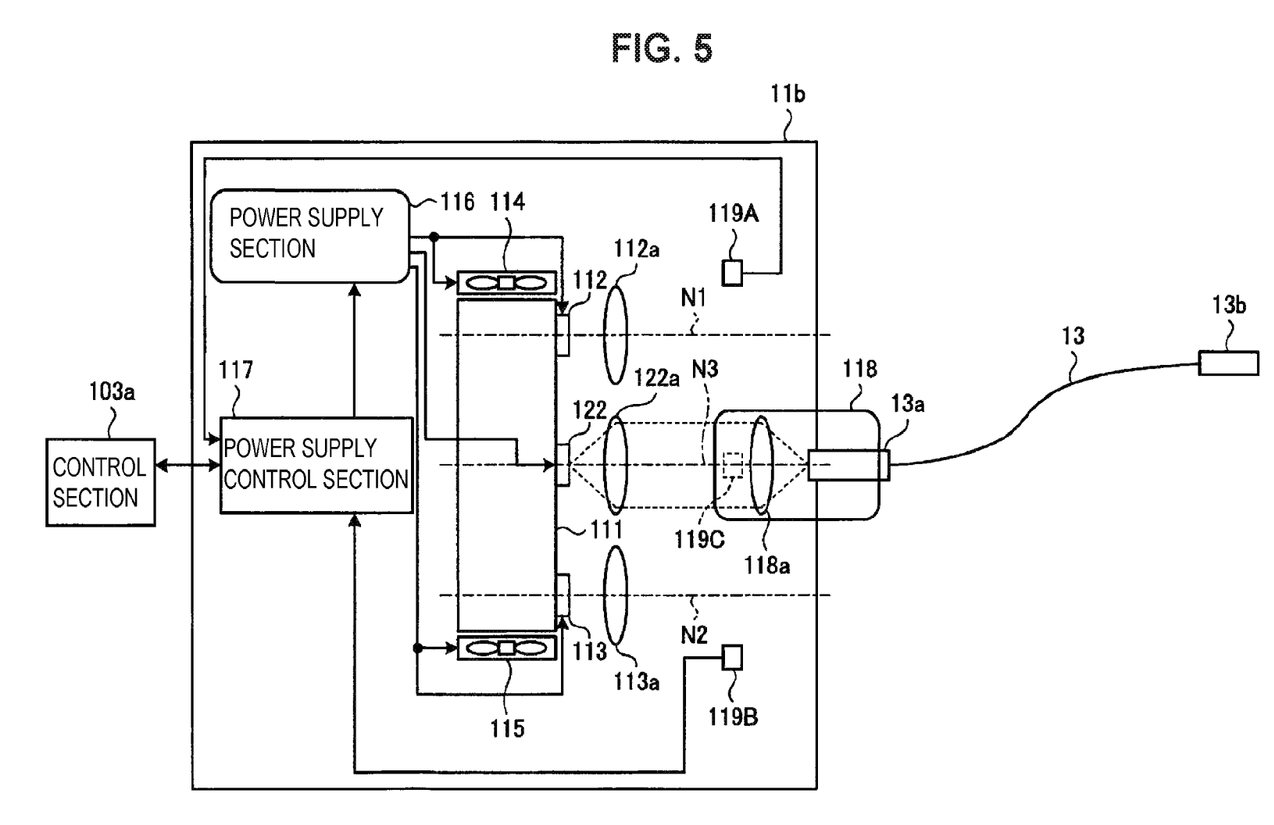
FIG. 5 is a schematic diagram illustrating a configuration of a light source device according to Modification 2 of Embodiment 1 of the present disclosure.

Next, Modification 2 of Embodiment 1 of the present disclosure will be described. FIG. 5 is a schematic diagram illustrating a configuration of a light source device according to Modification 2 of Embodiment 1 of the present disclosure. Note that the same configuration as that described above is denoted by the same reference numeral for description. Although the above-described Modification 1 gives description assuming that the plurality of light sources serving as the main light sources are arranged in a direction different from the movement direction of the light source switching section 118, in the Modification 2, the plurality of light sources (the first main light source 112 and the second main light source 122 in the Modification 2) serving as the main light sources are arranged along the movement direction of the light source switching section 118.

A light source device 11b according to the Modification 2 includes, in addition to the configuration of the light source device 11 according to the above-described Embodiment 1, the second main light source 122, the third collimator lens 122a, and a third detection sensor 119C. Note that also in the Modification 2, the first light source 112 is described as the first main light source 112.

The second main light source 122 is between the first main light source 112 and the second light source 113, side by side along the movement direction of the light source switching section 118. The third collimator lens 122a is provided on an optical path N3 of illumination light emitted by the second main light source 122. The third collimator lens 122a is disposed in a manner that its own focus position is located on a light-emitting surface of the second main light source 122, and converts illumination light emitted by the second main light source 122 into parallel light.

The third detection sensor 119C is implemented by using, for example, a photo-interrupter or a proximity sensor, and inputs a detection signal to the power supply control section 117 in the case where the light source switching section 118 comes close. The third detection sensor 119C is disposed at a position such that the third detection sensor 119C is close to the light source switching section 118 and generates a detection signal in the case where the light source switching section 118 is located at a position (third position) that is an intermediate position between the first position and the second position and is on an optical path of illumination light emitted by the second main light source 122.

The light source switching section 118 is disposed at one of the first position, the second position, and the third position. Also in the Modification 2, movement of the light source switching section 118 switches illumination light that enters the light guide 13 to illumination light emitted by one of the first main light source 112, the second main light source 122, and the second light source 113.

According to the Modification 2, an effect similar to that of the above-described Embodiment 1 can be obtained, and also, a wavelength band of illumination light to be emitted can be switched selectively in the main light source only by moving the light source switching section 118.

In addition, according to the Modification 2, an effect similar to that of the above-described Embodiment 1 can be obtained, and also, the heat sink 111 holding the first main light source 112 and the second light source 113 further holds the second main light source 122; thus, there is no need to additionally provide a heat sink, and the light source device 11b can be reduced in size as compared with Modification 1.

Embodiment 2

Figure 6:
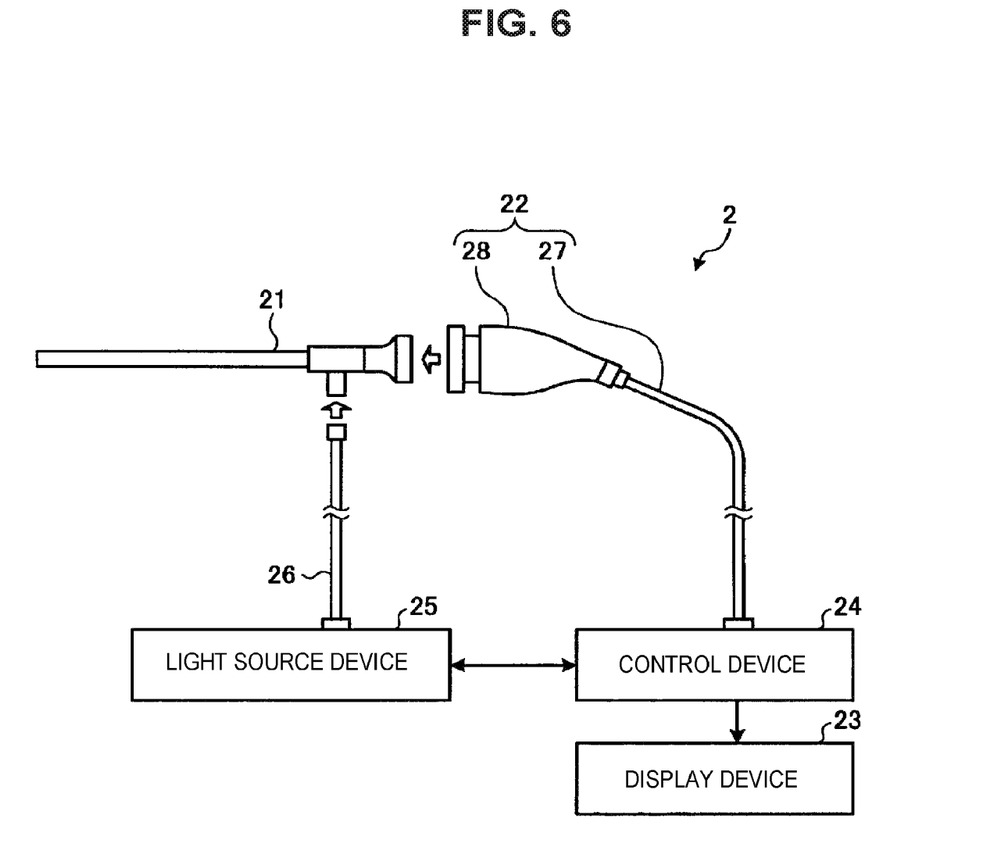
FIG. 6 illustrates a schematic configuration of an endoscope device according to Embodiment 2 of the present disclosure.

Now, Embodiment 2 of the present disclosure will be described. FIG. 6 illustrates a schematic configuration of an endoscope system according to Embodiment 2 of the present disclosure. An endoscope system 2 (medical observation system) illustrated in FIG. 6 is a device that is used in the medical field, and observes an object inside (the interior of a living body) an observation target such as a person. As illustrated in FIG. 6, this endoscope system 2 includes an endoscope 21, an imaging device 22, a display device 23, a control device 24 (image processing device), and a light source device 25 (medical light source device), and the imaging device 22 and the control device 24 constitute a medical image acquisition system. Note that in the Embodiment 2, the endoscope 21 and the imaging device 22 constitute an endoscope device using a rigid scope.

One end of a light guide 26 is connected to the endoscope 21, and the light source device 25 supplies illumination light for illuminating the interior of the living body to one end of the light guide 26. The light source device 25 includes the heat sink 111, the first light source 112, the second light source 113, the first fan 114, the second fan 115, the power supply section 116, the power supply control section 117, and the light source switching section 118 in the configuration of the light source device 11 of the above-described Embodiment 1, and also includes the light guide 26 in place of the light guide 13. Therefore, the light source device 25 has a configuration in which a light source of illumination light is switched by causing illumination light emitted by one light source, of illumination light emitted from two light sources, to enter an incident end of the light guide 26, and the light source switching section 118 that holds the incident end of the light guide 26 and includes the condenser lens 118a, which condenses illumination light on this light guide 26, can be moved to switch illumination light to be caused to enter the incident end. Note that the movement of the light source switching section 118 may be performed manually, or may be performed automatically under the control of the control device 24.

The light guide 26 is equivalent to the light guide 13 of the above-described Embodiment 1; one end is detachably connected to the light source device 25, and the other end is detachably connected to the endoscope 21. Thus, the light guide 26 transfers light supplied from the light source device 25 from the one end to the other end, and supplies it to the endoscope 21.

The imaging device 22 images an object image from the endoscope 21, and outputs a result of the imaging. As illustrated in FIG. 6, this imaging device 22 includes a transmission cable 27 serving as a signal transmission section and a camera head 28. In the Embodiment 2, the transmission cable 27 and the camera head 28 constitute a medical imaging device.

The endoscope 21, which is hard and has a slender shape, is inserted into the living body. Inside this endoscope 21 is provided an optical system that includes one or a plurality of lenses and condenses an object image. The endoscope 21 emits light supplied via the light guide 26 from a front end to apply it to the interior of the living body. Then, light applied to the interior of the living body (object image) is condensed by the optical system in the endoscope 21.

The camera head 28 is detachably connected to a base end of the endoscope 21. Thus, under the control of the control device 24, the camera head 28 images an object image condensed in the endoscope 21, and outputs an imaging signal obtained by the imaging.

One end of the transmission cable 27 is detachably connected to the control device 24 via a connector, and the other end is detachably connected to the camera head 28 via a connector. Specifically, the transmission cable 27 is a cable in which a plurality of electric wirings (not illustrated) are arranged inside an outer sheath, which is the outermost layer. The plurality of electric wirings are electric wirings for transmitting an imaging signal output from the camera head 28, and a control signal, a synchronization signal, a clock, and electric power output from the control device 24 to the camera head 28.

Under the control of the control device 24, the display device 23 displays an image generated by the control device 24. The display device 23 is preferably, but not limited to, one with a display section of 55 inches or more so that a sense of immersion is easily obtained in observation.

The control device 24 processes an imaging signal input from the camera head 28 via the transmission cable 27, and outputs an image signal to the display device 23, and also controls overall operation of the camera head 28 and the display device 23.

Also in the endoscope system 2 according to the Embodiment 2, movement of the light source switching section 118 switches illumination light that enters the light guide 26 to illumination light emitted by one of the first light source 112 and the second light source 113.

According to the above-described Embodiment 2, in the light source device 25 having a configuration in which a light source of illumination light is switched by causing illumination light emitted by one light source, of illumination light emitted from two light sources, to enter an end section (incident end) of the light guide 26, the light source switching section 118 that holds the end section of the light guide 26 and includes the condenser lens 118a is moved to switch illumination light to be caused to enter the end section of the light guide 26; thus, it is possible to switch a light source while suppressing an increase in size and complication of a device, as compared with a configuration in which a light source is moved by an actuator or the like as in a conventional configuration.

Embodiment 3

Figure 7:
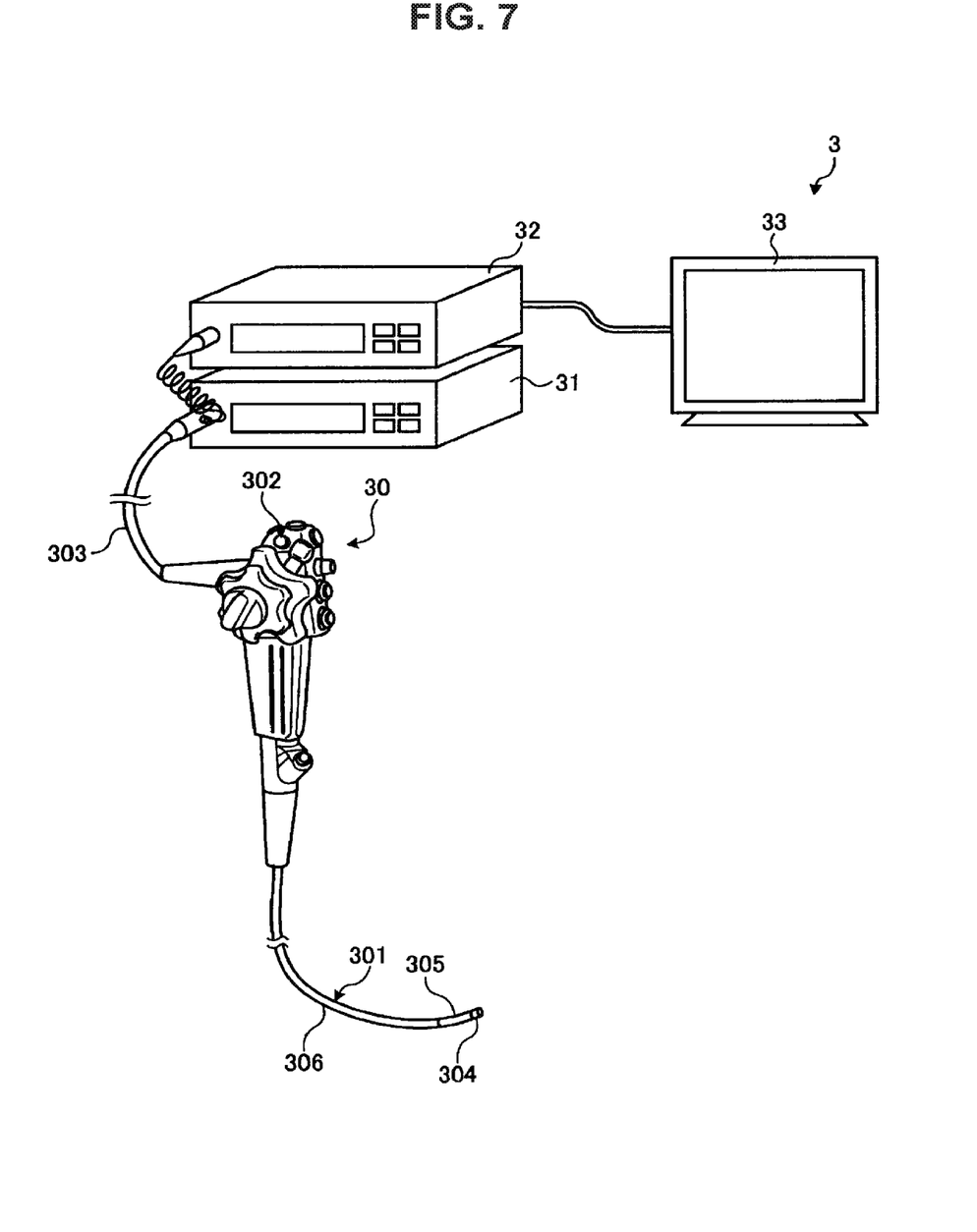
FIG. 7 illustrates a schematic configuration of an endoscope device according to Embodiment 3 of the present disclosure.

Now, Embodiment 3 of the present disclosure will be described. FIG. 7 illustrates a schematic configuration of an endoscope system according to Embodiment 3 of the present disclosure. Although the above-described Embodiment 2 describes the endoscope system 2 using a rigid scope as the endoscope 21, without limitation to this, an endoscope device using a flexible scope as an endoscope may be configured. The Embodiment 3 describes an example in the case where an imaging section is provided at a front end of an insertion section of a flexible endoscope.

An endoscope system 3 (medical observation system) includes an endoscope 30 (imaging device) that captures an internal image of an observation area by inserting an insertion section 301 into a subject and generates an electrical signal, a light source device 31 (medical light source device) that produces illumination light to be emitted from a front end of the endoscope 30, a control device 32 that performs predetermined image processing on an electrical signal acquired by the endoscope 30 and also controls overall operation of the entire endoscope system 3, and a display device 33 that displays an internal image subjected to image processing by the control device 32. By insertion of the insertion section 301 into a subject such as a patient, the endoscope system 3 acquires an internal image of the interior of the subject.

The endoscope 30 includes the insertion section 301 with a slender shape and flexibility, an operation section 302 that is connected to a base end side of the insertion section 301 and accepts input of various operation signals, and a universal cord 303 that extends in a direction different from a direction in which the insertion section 301 extends from the operation section 302 and includes various cables that are connected to the light source device 31 and the control device 32. The universal cord 303 includes a light guide that supplies illumination light from the light source device 31 to the endoscope 30.

The insertion section 301 includes a front end section 304 including an imaging section that captures an image of an object, a bendable bending section 305 including a plurality of bending pieces, and a long-length flexible tube section 306 with flexibility that is connected to a base end side of the bending section 305.

One end of the light guide is connected to the endoscope 30 by the universal cord 303, and the light source device 31 supplies illumination light for illuminating the interior of the living body to one end of the light guide. The light source device 31 includes the heat sink 111, the first light source 112, the second light source 113, the first fan 114, the second fan 115, the power supply section 116, the power supply control section 117, and the light source switching section 118 in the configuration of the light source device 11 of the above-described Embodiment 1, and also, the light guide 13 is provided in the universal cord 303. Therefore, the light source device 31 has a configuration in which a light source of illumination light is switched by causing illumination light emitted by one light source, of illumination light emitted from two light sources, to enter the incident end 13a of the light guide 13, and the light source switching section 118 that holds the incident end 13a of the light guide 13 and includes the condenser lens 118a can be moved to switch illumination light to be caused to enter the incident end 13a. Note that the movement of the light source switching section 118 may be performed manually, or may be performed automatically under the control of the control device 32. In addition, although description is given assuming that the light guide 13 is provided from the light source device 31 up to the universal cord 303, a light guide of the light source device 31 and a light guide of the universal cord 303 may be separately provided. For example, the following configuration may be adopted: the light guide 13 is provided in the light source device 31, and when the universal cord 303 is connected, an emission end of this light guide 13 faces or is connected to an incident end of a light guide that is inserted into the universal cord 303, so that illumination light can be suppled into the universal cord 303 from the light source device 31.

The light guide is equivalent to the light guide 13 of the above-described Embodiment 1; one end is detachably connected to the light source device 31, and the other end is detachably connected to the endoscope 30. Thus, the light guide transfers light supplied from the light source device 31 from the one end to the other end, and supplies it to the endoscope 30.

Also in the endoscope system 3 according to the Embodiment 3, movement of the light source switching section 118 switches illumination light that enters the light guide to illumination light emitted by one of the first light source 112 and the second light source 113.

According to the above-described Embodiment 3, in the light source device 31 having a configuration in which a light source of illumination light is switched by causing illumination light emitted by one light source, of illumination light emitted from two light sources, to enter an end section (incident end) of the light guide, the light source switching section 118 that holds the end section of the light guide and includes the condenser lens 118a is moved to switch illumination light to be caused to enter the end section of the light guide; thus, it is possible to switch a light source while suppressing an increase in size and complication of a device, as compared with a configuration in which a light source is moved by an actuator or the like as in a conventional configuration.

As described above, a medical light source device and a medical observation system according to the present disclosure are useful for switching a light source while suppressing an increase in size and complication of a device.

Additionally, the present technology may also be configured as below.

(1)
A medical light source device including:
a plurality of light sources; and
a light source switching section that holds an end section of a light guide that transmits light, and is capable of disposing the end section on one of optical paths of light emitted by the plurality of light sources.

(2)
The medical light source device according to (1), in which the plurality of light sources include a main light source and an auxiliary light source.

(3)
The medical light source device according to (2), in which the main light source and the auxiliary light source have substantially a same maximum luminance.

(4)
The medical light source device according to (3), in which the main light source and the auxiliary light source each emit white light.

(5)
The medical light source device according to any one of (1) to (4), further including
a collimator lens that makes light emitted by the light source into substantially parallel light,
in which the light source switching section includes a condenser lens that condenses the parallel light on the end section of the light guide.

(6)
The medical light source device according to (2), further including a power supply section that supplies electric power to the plurality of light sources,
in which the main light source and the auxiliary light source have different power supply systems.

(7)
The medical light source device according to any one of (1) to (6), further including
a heat sink that absorbs heat of the plurality of light sources.

(8)
A medical observation system including:
an imaging device that captures an enlarged image of a minute area of an object and generates an imaging signal;
a light guide that transmits illumination light to the imaging device; and
a medical light source device including
a plurality of light sources that emit the illumination light, and
a light source switching section that holds an incident end of the light guide, and disposes the incident end on one of optical paths of the illumination light emitted by the plurality of light sources, thereby switching the light source of illumination light that enters the light guide.

REFERENCE SIGNS LIST 1 surgical microscope system
2, 3 endoscope system
10 microscope device
11, 25, 31 light source device
12, 23, 33 display device
13, 26 light guide
13a incident end
13b emission end
21, 30 endoscope
22 imaging device
24, 32 control device
27 transmission cable
28 camera head
101 microscope section
102 support section
103 base section
103a control section
110 first main light source section
111 heat sink
112 first light source (first main light source)
112a first collimator lens
113 second light source
113a second collimator lens
114 first fan
115 second fan
116 power supply section
117 power supply control section
118 light source switching section
118a condenser lens
119A first detection sensor
119B second detection sensor
119C third detection sensor
120 second main light source section
121 second heat sink
122 second main light source
122a third collimator lens
123 third fan
130 third main light source section
131 third heat sink
132 third main light source
132a fourth collimator lens
133 fourth fan

The invention claimed is:

1. A medical light source device comprising:
a plurality of light sources; and
light source switching mechanism that holds an end portion of a light guide that transmits light, the light source switching mechanism being translatable between positions so that the end portion is in one of optical paths of light emitted by the plurality of light sources, wherein the light source switching mechanism includes a condenser lens to focus the light onto the end portion of the light guide, wherein an optical axis of the light guide is coaxial with an optical axis of a corresponding light source when the light guide is linearly translated into an optical path of light emitted by the corresponding light source for each light source of the plurality of light sources.

2. The medical light source device according to claim 1, wherein the plurality of light sources include a main light source and an auxiliary light source.

3. The medical light source device according to claim 2, wherein the main light source and the auxiliary light source have substantially a same maximum luminance.

4. The medical light source device according to claim 3, wherein the main light source and the auxiliary light source each emit white light.

5. The medical light source device according to claim further comprising
a power supply mechanism that supplies electric power to the plurality of light sources,
wherein the main light source and the auxiliary light source have different power supply systems.

6. The medical light source device according to claim 1, further comprising a collimator lens that makes light emitted by one of the plurality of light sources into substantially parallel light.

7. The medical light source device according to claim 1, wherein the light source switching mechanism includes:
a moving mechanism configured to move the condenser lens to one of a first position, in an optical path of a first one of the plurality of light sources, and a second position, in an optical path of a second one of the plurality of light sources,
the moving mechanism includes one of a linear guide and a rotary guide to guide a movement of the condenser lens, and
the moving mechanism includes a click mechanism having a spring, and the moving mechanism is configured to be moved by a force of the spring.

8. The medical light source device according to claim 1, further comprising:
a control circuit that selects one of the plurality of light sources; and
a power supply circuit that supplies electric power to only one of the plurality of light sources, which is the selected one of the plurality of light sources selected by the control circuit.

9. The medical light source device according to claim 8, further comprising:
a common heat sink that is thermally connected to each of the plurality of light sources;
a plurality of fans each attached to the common heat sink and each corresponding to a different one of the plurality of light sources, and
the power supply circuit is further configured to supply electric power to one of the plurality of fans, which is the one of the plurality of fans that corresponds to the selected one of the plurality of light sources selected by the control circuit.

10. The medical light source device according to claim 1, further comprising a common heat sink that is thermally connected to each of the plurality of light sources.

11. The medical light source device according to claim 10, wherein the common heat sink includes at least one of plate-like members stacked at predetermined intervals, rod-like members, and a bellows shape.

12. The medical light source device according to claim 1, wherein the light source switching mechanism is translatable along a direction that intersects the optical paths.

13. The medical light source device according to claim further comprising a collimator lens for each of the plurality of light sources.

14. The medical light source device according to claim 1, wherein optical axes of the plurality of light sources are parallel.

15. A medical observation system comprising:
an imaging device that captures an enlarged image of a minute area of an object and generates an imaging signal;
a light guide that transmits illumination light to the imaging device; and
a medical light source device including:
a plurality of light sources that emit the illumination light, and
light source switching mechanism that holds an end portion of the light guide, the light source switching mechanism being translatable between positions so that the end portion is in one of optical paths of the illumination light emitted by the plurality of light sources, thereby switching the light source of illumination light that enters the light guide, wherein the light source switching mechanism includes a condenser lens to focus the light onto the end portion of the light guide, wherein an optical axis of the light guide is coaxial with an optical axis of a corresponding light source when the light guide is linearly translated into an optical path of light emitted by the corresponding light source for each light source of the plurality of light sources.

16. The medical observation system according to claim 15, wherein
the medical light source device further includes a collimator lens that makes light emitted by one of the plurality of light sources into substantially parallel light,
the source switching mechanism includes
a moving mechanism configured to move the condenser lens to one of a first position, in an optical path of a first one of the plurality of light sources, and a second position, in an optical path of a second one of the plurality of light sources,
the moving mechanism includes one of a linear guide and a rotary guide to guide a movement of the condenser lens, and
the moving mechanism includes a click mechanism having a spring, and the moving mechanism is configured to be moved by a force of the spring.

17. The medical observation system according to claim 15, further comprising a common heat sink that is thermally connected to each of the plurality of light sources.

18. The medical observation system according to claim 15, wherein the light source switching mechanism is translatable along a direction that intersects the optical paths.

19. The medical observation system according to claim 15, further comprising a collimator lens for each of the plurality of light sources.

20. The medical observation system according to claim 15, wherein optical axes of the plurality of light sources are parallel.

* * * * *